United States Patent [19]

Sanderson et al.

[11] Patent Number: 5,099,073

[45] Date of Patent: Mar. 24, 1992

[54] CATALYTIC PROCESS FOR THE PRODUCTION OF DIKETONE DERIVATIVES OF POLYOXYPROPYLENE GLYCOLS

[75] Inventors: John R. Sanderson, Leander; John M. Larkin, Austin, both of Tex.

[73] Assignee: Texaco Chemical Company, White Plains, N.Y.

[21] Appl. No.: 653,220

[22] Filed: Feb. 11, 1991

[51] Int. Cl.$^5$ .................................. C07C 45/00
[52] U.S. Cl. ........................................ 568/405
[58] Field of Search .......................... 508/403, 405

[56] References Cited

U.S. PATENT DOCUMENTS

| | | | |
|---|---|---|---|
| 1,949,425 | 3/1934 | Lazier | 568/405 |
| 2,028,267 | 1/1936 | Archibald et al. | 568/403 |
| 2,794,053 | 5/1957 | Altreuter et al. | 568/403 |
| 2,829,165 | 4/1958 | Coussemant | 568/403 |
| 3,654,370 | 4/1972 | Yeakey | 564/480 |
| 3,981,921 | 9/1976 | Bohmholdt et al. | 568/403 |
| 4,141,919 | 2/1979 | Gremmelmaier | 568/403 |
| 4,980,514 | 12/1990 | Sanderson et al. | 568/405 |

FOREIGN PATENT DOCUMENTS

| | | | |
|---|---|---|---|
| 0043309 | 1/1982 | European Pat. Off. | 568/403 |
| 60-258135 | 12/1985 | Japan | 568/403 |

*Primary Examiner*—James H. Reamer
*Attorney, Agent, or Firm*—Jack H. Park; Kenneth R. Priem; Carl G. Ries

[57] ABSTRACT

A process for the conversion of a polyoxypropylene glycol to the corresponding diketone derivative by dehydrogenation in the presence of an unsupported nickel, copper, chromia catalyst or a Raney nickel catalyst.

2 Claims, No Drawings

CATALYTIC PROCESS FOR THE PRODUCTION OF DIKETONE DERIVATIVES OF POLYOXYPROPYLENE GLYCOLS

BACKGROUND OF THE INVENTION

1. Field of the Invention

This invention relates to an improved process for the production of diketones from polyoxypropylene glycols More particularly, this invention relates to a catalytic process for the substantially selective conversion of polyoxypropylene glycols to diketones wherein the polyoxypropylene glycol is brought into contact with catalyst selected from the group consisting of nickel, copper, chromium catalysts and Raney nickel at a temperature within the range of about 200° to about 260° C. and a pressure within the range of about atmospheric to about 5000 psig.

2. Prior Art

Process

An article in the *Journal of Organic Chemistry*, 151, 5482 (1986) discloses that alkanones can be prepared by refluxing an alkanol in solution in benzene or toluene in the presence of a Raney nickel catalyst.

Copending Sanderson application Ser. No. 444,211, filed Dec. 1, 1989 and entitled "Ketone Derivatives of Polyoxypropylene Glycols" (Docket No. 80,870), now U.S. Pat. No. 4,980,514 discloses the preparation of ketone terminated polyoxypropylene glycols by oxidizing the polyoxypropylene glycol with a hypochlorite in the presence of a ruthenium oxide catalyst and a bicarbonate.

Sanderson et al. U.S. Pat. No. 4,960,948, based on a U.S. patent application filed Dec. 26, 1989 and entitled "Manufacture of Ketone Derivatives of Polyoxypropylene Glycols", discloses the preparation of ketone terminated derivatives of polyoxypropylene glycols by oxidizing the polyoxypropylene glycol with a hypochlorite in solution in acetic acid.

Copending Sanderson et al. U.S. patent application Ser. No. 07/583,101, filed Sept. 17, 1990, and entitled "Catalyzed Reaction of Hypochlorites with Polyoxypropylene Glycols" now abandoned discloses the organic acid catalyzed reaction of hypochlorites with polyoxypropylene glycols to provide the corresponding ketone terminated derivatives.

Marion et al. U.S. Pat. No. 2,928,877 describe the low pressure vapor phase amination of oxyalkylene glycol monoalkyl ethers over a hydrogenation/dehydrogenation catalyst in a hydrogen atmosphere.

Shirley et al. U.S. Pat. No. 3,128,311 is directed to a high pressure process for the conversion of aliphatic alcohols to amines in the presence of ammonia and hydrogen using a catalyst composed of nickel, copper and a third component, which is preferably chromium oxide. The starting material for the Shirley et al. process is an aliphatic alcohol containing 1 to 20 carbon atoms. The reaction is conducted over a temperature range of about 180° to about 275° C. and in the presence of a comparatively large amount of added hydrogen. The partial pressure of hydrogen is in the range of 30% to 85% of the total pressure in the system. Shirley et al. use about 1 to about 8 moles of ammonia per mole of alcohol. The patentees report comparatively high yields of primary amines of about 55 to about 80% at conversions of the alcohol ranging from about 50 to about 95%.

Boettger et al. U.S. Pat. No. 4,014,933 disclosed the reaction of alcohols, including diols with ammonia or an amine at elevated temperatures and pressures in the presence of hydrogen using a catalyst composed of cobalt or nickel and iron.

In Yeakey U.S. Pat. No. 3,654,370 a process is disclosed for preparing polyoxyalkylene polyamines by reacting a corresponding polyol, such as a diol, with ammonia at elevated temperatures and pressures in the presence of a catalyst composed of nickel, copper and chromia.

Hauptman and Welter, Chem. Rev., 62, 347 (1962) disclose that thiols and thioethers, both alkyl and aryl can be desulfurized by hydrogenolysis with Raney nickel.

"Synthetic Reagents", Vol. 4, p. 170, discloses that Raney nickel is used to selectively reduce olefin in the presence of a variety of functional groups.

Mitchell and Lai, *Tetrahedron Lett.*, 21, 2637 (1980) disclose that Raney nickel has been used to reduce the carbonyl of aldehydes and ketones to methylene.

Catalyst

Godfrey U.S. Pat. No. 3,037,025 discloses the preparation of N-alkyl substituted piperazines using catalyst compositions consisting of the metals and oxides of copper, nickel and cobalt (including mixtures thereof) which may also be promoted by the inclusion of a normally non-reducible metal oxide such as chromium, aluminum, iron, calcium, magnesium, manganese and the rare earths. Preferred catalyst compositions are indicated as containing from about 44 to about 74 wt.% of nickel, about 5 to about 55 wt.% of copper and about 1 to about 5 wt.% of chromia.

Moss U.S. Pat. No. 3,151,112 discloses catalyst compositions useful for the preparation of morpholines including one or more metals from the group including copper, nickel, cobalt, chromium, molybdenum, manganese, platinum, palladium and rhodium, which may also be promoted with normally nonreducible oxides such as chromium oxide, molybdenum oxide and manganese oxide. Representative catalyst compositions include those containing from about 60 to about 85 wt.% of nickel, about 14 to about 37 wt.% of copper and about 1 to about 5 wt.% of chromia. Nickel, copper, chromia catalysts are also disclosed in Moss U.S. Pat. No. 3,151,115 and Moss U.S. Pat. No. 3,152,998.

Winderl et al. U.S. Pat. No. 3,270,059 teaches the use of catalysts containing a metal of groups I-B and VIII of the Periodic System. Examples of suitable catalysts are stated to be copper, silver, iron, nickel, and particularly, cobalt.

Boettger et al. U.S. Pat. No. 4,014,933 discloses catalysts containing cobalt and nickel promoted with copper such as those containing from about 70 to about 95 wt.% of a mixture of cobalt and nickel and from about 5 to about 30 wt.% of copper.

Habermann U.S. Pat. No. 4,152,353 discloses catalyst compositions comprising nickel, copper and a third component which may be iron, zinc, zirconium or a mixture thereof such as catalysts containing from about 20 to about 49 wt.% of nickel, about 36 to about 79 wt.% of copper and about 1 to about 15 wt.% of iron, zinc, zirconium or a mixture thereof. Similar catalyst compositions are mentioned in Habermann U.S. Pat. No. 4,153,581.

European patent application 0017651 filed Oct. 20, 1980, contains a disclosure of catalyst compositions related to those disclosed by Habermann, such catalyst compositions being composed of nickel or cobalt, copper and iron, and zinc or zirconium such as compositions containing 20 to 90% cobalt, 3 to 72% copper and 1 to 16% of iron, zinc or zirconium and catalyst compositions containing 20 to 49% nickel, 36 to 79% copper and 1 to 16% of iron, zinc or zirconium.

German Offen. 2,271,033 discloses a catalyst composition containing 35% nickel, about 87.5% iron and a minor amount of chromia.

Johansson et al. U.S. Pat. No. 3,766,184 discloses catalyst compositions composed of iron and nickel and/or cobalt.

British Pat. No. 934,636 of Paul et al. entitled "Process for Preparing Oxyalkyleneamines" relates to a process for reacting a glycol ether with an amine such as ammonia in vapor phase in the presence of hydrogen and a nickel or cobalt catalyst deposited on a siliceous support.

Renken U.S. Pat. No. 4,642,303 discloses nickel, copper, chromia, iron catalysts supported on silica. The Renken application states that the catalyst is useful in promoting reactions such as the conversion of hydroxy-containing feedstocks to the corresponding acyclic, cyclic, or heterocyclic amines.

Sanderson et al. U.S. Pat. No. 4,704,482, entitled "Catalytic Purification of Tertiary Butyl Alcohol", discloses the use of unsupported or silica supported nickel, copper, chromia, iron oxide catalysts to reduce peroxide and hydroperoxide contaminants present in tert. butyl alcohol.

Vogel's *Textbook of Organic Chemistry*, 4th Ed., p. 303 discloses that Raney nickel catalyst is used for hydrogenation at low pressure and temperature. A special alloy is prepared by the fusion of equal parts of aluminum and nickel at 1200°-1500° C. This alloy is then treated with alkali which dissolves the aluminum and leaves the nickel. It is possible to prepare catalysts which vary in surface area by dissolving more or less of the aluminum out of the alloy. When all of the aluminum is removed, a very high surface area catalyst is obtained.

SUMMARY OF THE INVENTION

It has been discovered in accordance with the present invention that polyoxypropylene glycols can be converted to ketone terminated derivatives by the process described herein using a catalyst selected from the group consisting of nickel, copper, chromia catalysts and Raney nickel catalysts.

The feed material for the present invention is a polyoxypropylene glycol having an average molecular weight of about 130 to about 4,000, and more preferably, about 200 to about 2,000, of formula (I):

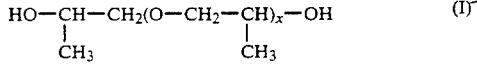

wherein x is an integer having a value of about 1 to about 70.

Examples of such polyoxypropylene glycols include commercial products such as a polyoxypropylene glycol having an average molecular weight of about 200, a polyoxypropylene glycol having an average molecular weight of about 500, a polyoxypropylene glycol having an average molecular weight of about 2000, a polyoxypropylene glycol having an average molecular weight of about 4,000, etc.

The reaction is suitably conducted under comparatively moderate conditions of temperature of about 200° to about 260° C. and at a pressure of about atmospheric to about 5000 psig. total pressure.

The dehydrogenation catalyst to be used in accordance with the present invention consists essentially of Raney nickel on an unsupported nickel, copper, chromium catalyst. The preferred catalyst for use in this process is one containing nickel, copper and chromium. The catalyst is described in U.S. Pat. No. 3,152,998 and U.S. Pat. No. 3,654,370. It is prepared by the reduction of a mixture of the oxides of nickel, copper and chromium in the presence of hydrogen at a temperature of 250° to 400° C. On an oxide-free basis the catalyst contains 60–85 mole % nickel, 14–37 mole % copper and 1–5 mole % chromium. A particularly preferred composition is one containing 70–80 mole % nickel, 20–25 mole % copper and 1–5 mole % chromium.

The process of the present invention may be conducted batchwise using an autoclave containing powdered catalyst, or it may be conducted continuously by passing the feed materials over a bed of pelleted catalyst.

Normally, the desired diketone can be recovered from the reaction mixture without distillation. Fractional distillation may be necessary with lower molecular weight feedstocks.

DETAILED DESCRIPTION OF THE PREFERRED EMBODIMENT OF THE PRESENT INVENTION

The present invention is further illustrated by the following specific examples which are given by way of illustration and which are not intended as limitations on the scope of this invention.

Procedure

A series of continuous runs was made using a polyoxypropylene glycol having an average molecular weight of about 2000 as a feedstock. The reactor was a 29½×0.51" stainless steel tube. The catalyst bed was 100 cc and contained pellets of the catalyst to be evaluated. Liquid feed was pumped through the bottom of the reactor. Pressure regulation was with a Skinner Uniflow valve and a Foxboro controller. Liquid was pumped with a Ruska pump. The reactor was electrically heated. 100–200 cc Prerun was collected at each temperature and then 100–200 cc material for analysis. The catalysts that were evaluated and the results are shown in the attached tables.

TABLE A

| Dehydrogenation of PPG in a 100-cc Tubular Reactor | | | | | | | | |
|---|---|---|---|---|---|---|---|---|
| N.B. No. | Polyol | Catalyst | Rate (cc/hr) | Pressure (psig) | Temp (°C.) | OH No. (mg/g) | Acid No. (mg/g) | Water (wt. %) |
| 6495-65-1 | PPG-2000 | Ni/Cu/Cr | 100 | 100 | 220 | 38 | 0.63 | 0.16 |
| 6495-65-2 | | | | | 240 | 22.1 | 1.01 | 0.16 |
| 6495-65-3 | | | | | 260 | 15.4 | 0.24 | 0.216 |
| 6495-65-4 | | | | | 280 | 14.5 | 1.43 | 1.66 |

TABLE A-continued

Dehydrogenation of PPG in a 100-cc Tubular Reactor

| N.B. No. | Polyol | Catalyst | Rate (cc/hr) | Pressure (psig) | Temp (°C.) | OH No. (mg/g) | Acid No. (mg/g) | Water (wt. %) |
|---|---|---|---|---|---|---|---|---|
| 6495-81-1 | PPG-2000 | Ni/Cu/Cr New charge | 100 | 100 | 200 | 44.6 | 0.78 | 0.167 |
| 6495-81-2 | | | | | 220 | 23.4 | 1.64 | 0.141 |
| 6495-81-3 | | | | | 240 | 26.6 | 1.18 | 0.183 |
| 6495-81-4 | | | | | 260 | 23.2 | 1.35 | 0.176 |
| 6495-82-1 | PPG-2000 | Continued from above | 50 | 100. | 200 | 44.1 | 0.28 | 0.163 |
| 6495-82-2 | | | | | 220 | 22.4 | 0.60 | 0.257 |
| 6495-82-3 | | | | | 240 | 14.3 | 0.47 | 0.214 |
| 6495-82-4 | | | | | 260 | 8.03 | 0.93 | 0.165 |
| 6495-83-1 | PPG-2000 | Continued from above | 100 | 500 | 200 | 65.3 | 0.64 | 0.196 |
| 6495-83-2 | | | | | 220 | 53.8 | 0.62 | 0.180 |
| 6495-83-3 | | | | | 240 | 30.9 | 1.11 | 0.213 |
| 6495-83-4 | | | | | 260 | 33.9 | 1.12 | 0.144 |
| 6495-96-1 | PPG-2000 | Ni/Cu/Cr New charge | 100 | 100 | 220 | 34.0 | 1.84 | 2.42 |
| 6495-96-2 | | | | | 240 | 25.8 | 1.23 | 0.387 |
| 6495-96-3 | | | | | 260 | 7.16 | — | 0.293 |
| 6495-97-1 | PPG-2000 | Ni/Cu/Cr | 100 | 100 | 220 | 36.7 | 1.16 | 0.871 |
| 6495-97-2 | | Same catalyst | | | 240 | 23.9 | 1.06 | 0.275 |
| 6495-97-3 | | Different lot # | | | 260 | 17.8 | — | 0.131 |
| 6495-66-1 | PPG-2000 | Ni/Cu/Cr/Fe on Kgr | 100 | 100 | 220 | — | — | — |
| 6495-66-2 | | | | | 240 | 26.4 | 1.11 | 0.357 |
| 6495-66-3 | | | | | 260 | 36.9 | 1.29 | 0.141 |
| 6495-66-4 | | | | | 280 | 26.5 | 2.19 | 0.082 |

TABLE B

Dehydrogenation of PPG in a 100-cc Tubular Reactor

| N.B. No. | Polyol | Catalyst | Rate (cc/hr) | Pressure (psig) | Temp (°C.) | OH No. (mg/g) | Acid No. (mg/g) | Water (wt. %) |
|---|---|---|---|---|---|---|---|---|
| 6495-44-1 | PPG-2000 | Ni/Cu/Cr on Al$_2$O$_3$ | 100 | 100 | 220 | 52.82 | 0.095 | 0.597 |
| 6495-44-2 | | | | | 240 | 45.30 | 0.88 | 0.465 |
| 6495-44-3 | | | | | 260 | 55.3 | 1.05 | 0.783 |
| 6495-44-4 | | | | | 280 | 56.5 | 1.46 | 1.274 |
| 6495-64-1 | PPG-2000 | Ni/Cu/Cr on Al$_2$O$_3$ | 100 | 100 | 160 | 87 | 0.28 | 0.39 |
| 6495-64-2 | | Mo promoted | | | 180 | 56 | 0.80 | 0.20 |
| 6495-64-3 | | | | | 200 | 48 | 0.62 | 0.55 |
| 6495-64-4 | | | | | 220 | 32 | 0.55 | 0.62 |
| 6495-43-1 | PPG-2000 | Ni/Cu/Cr on Al$_2$O$_3$ | 100 | 100 | 220 | 29.2 | 1.60 | 1.87(?) |
| 6495-43-2 | | Mo promoted | | | 240 | 43.0 | 1.20 | 0.40 |
| 6495-43-3 | | | | | 260 | 46.0 | 2.62 | 0.19 |
| 6495-43-4 | | | | | 280 | 36.0 | 2.39 | 0.16 |
| 6495-73-1 | PPG-2000 | 0.5% Ru on C | 100 | 100 | 220 | 85.2 | 0.77 | 0.432 |
| 6495-73-2 | | | | | 240 | 84.4 | 0.50 | 0.432 |
| 6495-73-3 | | | | | 260 | 88.6 | 0.30 | 0.488 |
| 6495-73-4 | | | | | 280 | 101.0 | 0.74 | 0.584 |
| 6495-74-1 | PPG-2000 | Copper Chromite | 100 | 100 | 220 | 49.6 | 3.54 | 0.582 |
| 6495-74-2 | | 80% CuO, 20% Cr$_2$O$_3$, | | | 240 | 48.1 | 4.88 | 0.686 |
| 6495-74-3 | | 1/16" pellets | | | 260 | 41.1 | 16.3 | 1.896 |
| 6495-74-4 | | | | | 280 | 44.6 | 9.28 | 0.076 |
| 6465-65-1 | PPG-2000 | Copper Chromite | 100 | 100 | 200 | 62.3 | 0.83 | 0.830 |
| 6465-65-2 | | 46% CuO, 46% Cr$_2$O$_3$, | | | 220 | 56.3 | 0.64 | 0.221 |
| 6465-65-3 | | 4% MnO$_2$ | | | 240 | 50.2 | 0.42 | 0.201 |
| 6465-65-4 | | | | | 260 | 44.9 | 1.49 | 0.376 |
| 6465-65-5 | | | | | 280 | 40.7 | 2.80 | 0.693 |
| 6465-65-6 | | | | | 300 | 25.1 | 1.25 | 0.504 |

Discussion of Table A and Table B

Run 6495-65 was the first run with the Ni/Cu/Cr catalyst. The optimum temperature appeared to be 260° C. Above 260° C. there was extensive decomposition as evidenced by the jump in acid number and the jump in the percent water present.

The reactor was recharged with the same catalyst 6495-81 and the reaction conducted at 200°-260° C. Optimum temperature here appeared to be 240°-260° C. The reaction was continued 6495-82 (using the same catalyst) and runs made again at 200°-260° C. Again, the optimum temperature is at 260° C. The reaction was continued over several days and again examined at 200°-260° C. 6495-83 Optimum temperature is again at 240°-260° C., but the catalyst appears to lose activity after long continuous use.

Run 6495-96 is a new charge of the same catalyst and excellent results are obtained at 260° C.

Run 6495-97 is a new charge of the same type of catalyst, but with slightly lower activity. The reason for the slight difference in results is probably due to differences in surface area.

Run 6495-66 was with a Ni/Cu/Cr/Fe on kieselguhr catalyst and it gave only fair results.

Table B continues other catalysts for comparison with the Ni/Cu/Cr catalyst of this invention and these include:

Ni/Cu/Cr on Al$_2$O$_3$
Ni/Cu/Cr on Al$_2$O$_3$ Mo promoted
0.5% Ru on C
Copper chromite None of the catalysts give results which are as good as the results obtained with unsupported Ni/Cu/Cr catalyst. It is especially surprising that the copper chromite catalyst gives such poor results since it is known in the art that copper chromite catalysts are good dehydrogenation catalysts.

Turning now to the tables, it is to be noted that the catalyst of the present invention was used in the following runs:
6495-65

TABLE C

Dehydrogenation of PPG in a 100-cc Tubular Reactor

| N.B. No. | Polyol | Catalyst | Rate (cc/hr) | Pressure (psig) | Temp (°C.) | OH No. (mg/g) | Acid No. (mg/g) | Water (wt. %) |
|---|---|---|---|---|---|---|---|---|
| 6465-76-1 | PPG-2000 | Copper Chromite | 100 | 100 | 220 | 55.92 | 1.35 | 0.073 |
| 6465-76-2 | | ⅛" tablets, 42% CuO, | | | 240 | 48.20 | 1.08 | 0.148 |
| 6465-76-3 | | 44% Cr$_2$O$_3$, 9% BaO | | | 260 | 41.1 | 0.86 | 0.363 |
| 6465-76-4 | | | | | 280 | 40.2 | 2.46 | 0.718 |
| 6465-91-1 | PPG-2000 | Copper Chromite | 100 | 100 | 220 | 52.49 | 0.99 | 0.0296 |
| 6465-91-2 | | ⅛" tablets, 27% CuO, | | | 240 | 47.25 | 0.92 | 0.179 |
| 6465-91-3 | | 32% Cr$_2$O$_3$, 6% BaO | | | 260 | 54.88 | 1.09 | 0.341 |
| 6495-86-1 | PPG-2000 | 0.5% Rh on Al$_2$O$_3$, | 100 | 100 | 220 | 65.0 | 0.11 | 0.283 |
| 6495-86-2 | | 1/16" pellets | | | 240 | 67.0 | 0.48 | 0.331 |
| 6495-86-3 | | | | | 260 | 61.0 | 1.39 | 0.488 |
| 6495-86-4 | | | | | 280 | 75.2 | 2.70 | 1.382 |

Comparison catalysts continue in Table C. None of the copper chromite catalysts in Table C were as good as the Ni/Cu/Cr catalyst of this invention—and in fact, most are very poor catalysts for dehydrogenation of PPG. 0.5% Rh on alumina is also a very poor catalyst. All of these catalysts give <25% conversion under optimum conditions.

Raney Nickel

Table D shows runs with three different grades of Raney nickel. Under optimum conditions, conversions as high as 75% could be obtained. There is very little dehydration to olefin or oxidation to acid as evidenced by the low percent water and low acid number.

6495-81
6495-82
6495-83
6495-96
6495-97

Significant conversion of the PPG-2000 to the diketone derivatives was obtained; the conversion increasing with increases in the reaction temperature. The reaction products had comparatively low acid numbers and water contents. Good results were also obtained with a Raney nickel catalyst. Mixed results were obtained with the other catalysts.

Note that satisfactory conversions (as measured by hydroxyl number) were obtained with the catalysts of

TABLE D

Runs with Raney Nickel

| N.B. No. | Polyol | Catalyst | Rate (cc/hr) | Pressure (psig) | Temp (°C.) | OH No. (mg/g) | Acid No. (mg/g) | Water (wt. %) |
|---|---|---|---|---|---|---|---|---|
| 6495-79-1 | PPG-2000 | Raney Granular Nickel | 100 | 100 | 220 | 31.3 | 0.92 | 0.616 |
| 6495-79-2 | | 8 × 12 mesh, Surface | | | 240 | 25.5 | 0.98 | 0.189 |
| 6495-79-3 | | area = 31 m$^2$/g | | | 260 | 15.7 | 0.30 | 0.259 |
| 6495-79-4 | | | | | 280 | 25.7 | 1.09 | 0.466 |
| 6528-23-1 | PPG-2000 | Raney Granular Nickel | 100 | 100 | 200 | 33.6 | 0.59 | 0.78 |
| 6528-23-2 | | 8 × 12 mesh, Surface | | | 220 | 16.6 | 0.76 | 0.26 |
| 6528-23-3 | | area = 19 m$^2$/g | | | 240 | 14.1 | 0.94 | 0.11 |
| 6528-23-4 | | | | | 260 | 16.9 | 0.77 | 0.19 |
| 6528-43-1 | PPG-2000 | Raney Granular Nickel | 100 | 100 | 200 | 23.5 | — | 0.40 |
| 6528-43-2 | | 8 × 12 mesh, Surface | | | 220 | 17.7 | 0.33 | 0.15 |
| 6528-43-3 | | area = 22 m$^2$/g | | | 240 | 22.5 | 0.32 | 0.17 |
| 6528-43-4 | | | | | 260 | 25.4 | 0.43 | 0.29 |

It is to be observed that the hydroxyl number of the PPG-2000 starting material was 57.0. Cracking of the PPG-2000 is indicated when the reaction product has a hydroxyl number of more than 57. The extent to which the PPG-2000 was converted to the desired diketone product is indicated by the extent to which the hydroxyl number of the reaction product was lowered (the lower the hydroxyl number the greater the conversion).

The PPG starting material had an acid number of about zero. An increase in the acid number of the reaction product is a measure of the extent to which the terminal hydroxyl groups of the PPG-2000 were converted to undesired carboxyl acid groups rather than the desired ketone groups.

Dehydration of the PPG-2000 leads to the formation of undesired by-products. Therefore, the wt.% of water in the reaction product is a measure of the extent to which undesired dehydration of the PPG-2000 occurs.

the present invention in runs 6495-69-1, 6495-81-2, 6495-96-1 and 6495-97-1, but that the use of an alumina support for the catalyst resulted in the formation of a reaction product characterized by low conversion to the diketone derivative.

When a modified supported nickel, copper, chromia, molybdenum catalyst was used, satisfactory results were obtained at a reaction temperature of 220° C. (6495-64-4). Note, however, that unsatisfactory results were obtained at lower temperatures (6495-64-1 and 6495-64-2).

In run 6495-43-1, using a phosphorus-promoted alumina support for the catalyst resulted in excessive dehydration at 220° C. In contrast to the results shown in Table A, an increase in reaction temperature resulted in increased undesirable production of carboxylic acid derivatives of decreased production of the desired diketone derivatives (see table).

The use of a ruthenium on activated carbon catalyst resulted in undesirable cracking (6495-73-1).

The use of a chromia supported copper oxide catalyst in run 6495-74-1 resulted in an undesirable conversion of the PPG-2000 to carboxylic acid derivatives whereas there was only a minor conversion of the PPG-2000 to the desired diketone derivatives in runs 6465-65-2, 6475-76-1, 6465-91-1 and 6495-1-1.

In run 6495-86-1, the use of an alumina supported rhenium catalyst resulted in cracking of the PPG-2000 feedstock.

The foregoing examples are given by way of illustration only and are not intended as limitations on the scope of this invention, which is defined by the appended claims.

We claim:

1. A process for the conversion of a polyoxypropylene glycol having an average molecular weight of about 200 to about 2,000 to the corresponding polyoxypropylene diketone which comprises the steps of:

contacting said polyoxypropylene glycol with a catalyst under dehydrogenation conditions to thereby convert at least a portion of said polyoxypropylene glycol to said polyoxypropylene diketone, and recovering said polyoxypropylene diketone from the products of the reaction, said reductive dehydrogenation conditions including a temperature within the range of about 200° to about 260° C and a pressure within the range of about atmospheric to about 5000 psig., said catalyst consisting essentially of an unsupported nickel, copper, chromia catalyst containing from about 60 to about 85 mole percent of nickel, about 14 to 37 mole percent of copper and about 1 to 3 mole percent of chromia.

2. A method as in claim 1 wherein the catalyst consists essentially of from about 72 to about 78 mole percent of nickel, about 20 to about 25 mole percent of copper and about 1 to about 3 mole percent of chromia.

* * * * *